United States Patent [19]

Reck et al.

[11] Patent Number: 4,608,051
[45] Date of Patent: Aug. 26, 1986

[54] AUDITORY CANAL WALL PROSTHESIS AND PROCESS FOR PRODUCING SAME

[75] Inventors: Ralf Reck, Mainz-Bretzenheim; Heinz Broemer, Wetzlar-Hermannstein; Klaus Deutscher, Wetzlar; Henning Franek, Braunfels-Tiefenbach, all of Fed. Rep. of Germany

[73] Assignee: Ernst Leitz Wetzlar GmbH, Wetzlar, Fed. Rep. of Germany

[21] Appl. No.: 459,696

[22] PCT Filed: Apr. 29, 1982

[86] PCT No.: PCT/DE82/00092
§ 371 Date: Dec. 29, 1982
§ 102(e) Date: Dec. 29, 1982

[87] PCT Pub. No.: WO82/03765
PCT Pub. Date: Nov. 11, 1982

[30] Foreign Application Priority Data

Apr. 29, 1981 [DE] Fed. Rep. of Germany ....... 3117025
Mar. 26, 1982 [DE] Fed. Rep. of Germany ....... 3211212

[51] Int. Cl.$^4$ .............................................. A61F 2/18
[52] U.S. Cl. ..................................... 623/10; 128/92 C
[58] Field of Search ............................... 3/1, 1.9, 1.91; 128/92 C, 92 G, 1 R

[56] References Cited

U.S. PATENT DOCUMENTS 3,922,155 11/1975 Brömer et al. .
4,135,935 1/1979 Pfeil et al. .
4,473,909 10/1984 Reck et al. .

FOREIGN PATENT DOCUMENTS 1562999 9/1976 United Kingdom .

Primary Examiner—Richard J. Apley
Assistant Examiner—David J. Isabella
Attorney, Agent, or Firm—Schwartz, Jeffery, Schwaab, Mack, Blumenthal & Evans

[57] ABSTRACT

Prosthesis for the partial or complete reconstruction of the rear auditory canal wall, with a hollow cylindrical sleeve shape (1), not closed, and having at least in its two base areas (9) and (10) differential expansions in the manner of a hyperboloid with a preferentially elliptic cross section. A bioactive substance is used as the material. The inner wall of the prosthesis has a positive or negative (spatial) coordinate grid (6, 7). Selected partial surface areas (11, 12; 4) may be provided with an insoluble, bio-inert protective layer. The latter may consist of an additive protective layer (S(+)) or a substractive protective layer (S(−)). Appropriate coating processes are cited for both of these variants. When S(−) layers are produced, these may be exposed to a subsequent sealing and/or silanizing treatment.

35 Claims, 10 Drawing Figures

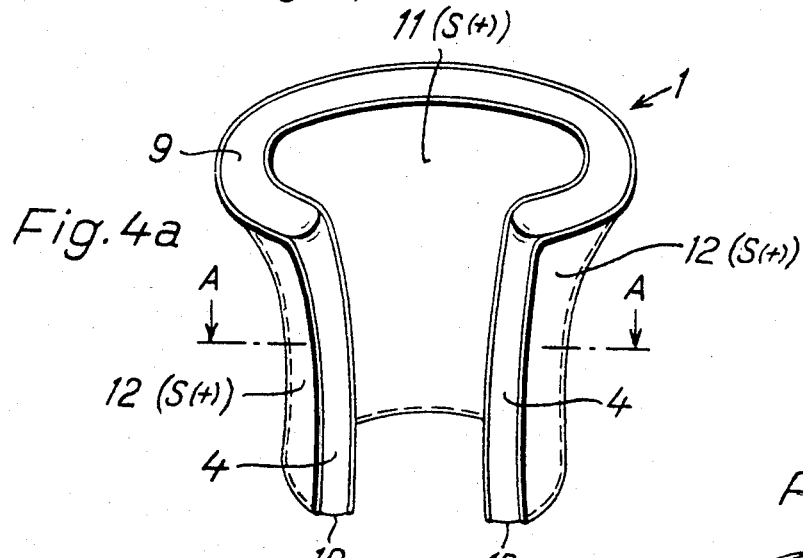
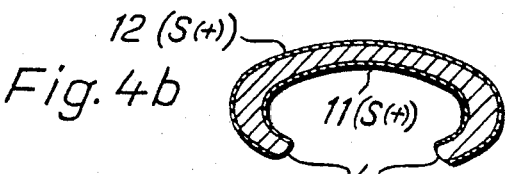
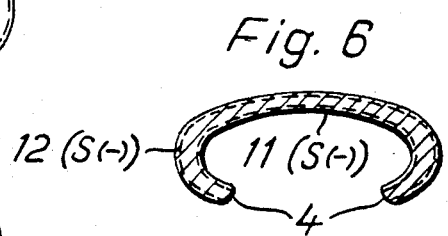
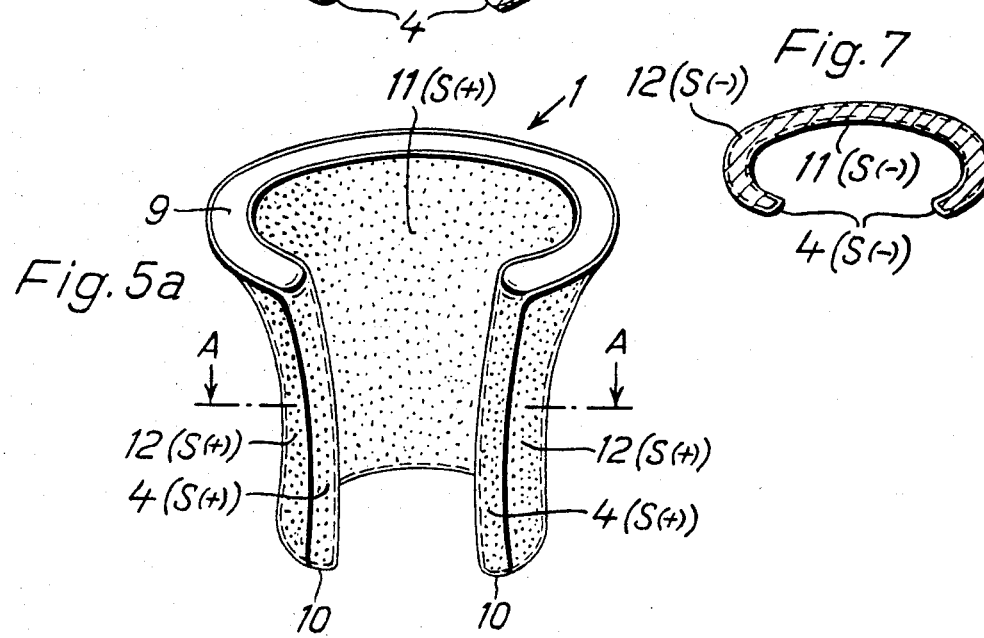
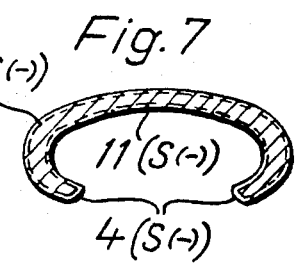
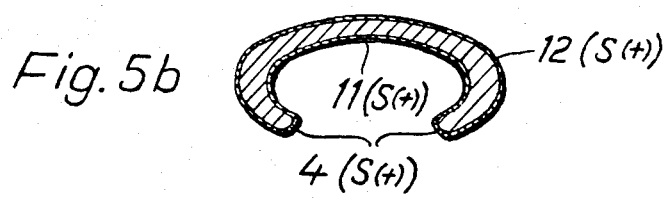

AUDITORY CANAL WALL PROSTHESIS AND PROCESS FOR PRODUCING SAME

BACKGROUND OF THE INVENTION

The invention concerns a prosthesis for the total or partial replacement of the rear auditory canal wall together with a process for producing same.

Due to pathological conditions, it may be necessary to replace a part of the rear auditory canal wall, or even the entire rear auditory canal tract, by a permanent implant.

SUMMARY OF THE INVENTION

It is therefore an object of the present invention to provide a prosthesis form similar to the actual anatomical conditions, to select an optimum material for the prosthesis, and to provide on the prosthesis means for the anatomically and geometrically accurate alignment and positioning of the prosthesis at the location of the implantation. It is a further object of the invention to design the partial areas of the surface of the prosthesis not intended for actual bonding with the bone (fusing zone: an implant/osseous hard tissue), so that they will be biochemically entirely resistant and bioinactive. Another object is to provide a process for the subsequent bioinactivation of selected partial areas of prostheses or parts of prostheses which are bioactive.

The object of the invention is attained with a prosthesis of the aforementioned type according to the invention in that the prosthesis is in the form of an open hollow cylindrical sleeve having a cut-out selection and having hyperboloid-shaped differential expansions at least in its two base areas wherein the expansions preferably have elliptical cross sections and wherein the prosthesis comprises bioactive material. According to a particular embodiment, the inner wall is provided with a spatial coordinate grid. The grid may consist of two families of lines crossing each other, with one of the families comprising a plurality of hyperbolic lines extending essentially in the direction of the axis of the sleeve and the other of a plurality of elliptic lines extending essentially perpendicularly to the axis of the sleeve. The lines of the coordinate grid may be in the form of groove-like depressions of any cross-sectional shape, for example, triangular, rectangular, rounded, etc. It is also possible to provide the lines of the coordinate grid in the form of bead-like projections. According to a further form of embodiment of the invention, in place of continuous lines, discontinuous, periodically, arranged grid elements, for example, small pits or knobs, may be provided. It is advantageous in this case to produce the positive embodiments of the grid from the material of the prosthesis itself. The mean mesh width of the coordinate grid is between 1 and 2 mm. Advantageously, the length of the sleeve's cut-out section is greater than its means circumferential distance, and the shortest of all of the principal axes of internal ellipses produced by sections perpendicular to the axis of the sleeve is longer than the mean circumferential distance of the sleeve's cut-out section. Dimensioning may be effected so that the length of the sleeve continuously increases toward the two cuts where the sleeve's cut-out section has been cut and reaches a maximum there, while its minimum is attained at the sleeve area opposite the cut-out section. According to a particular embodiment, of the present invention, the wall thickness of the sleeve is between 0.5 and 2.0 mm, the average length of the sleeve between 12 and 25 mm, the mean circumferential distance of the sleeve's cut-out section between 7 and 14 mm, the mean length of the principal axes of the ellipses between 10 and 17 mm, the mean length of the secondary axes between 5 and 8 mm, and the positive or negative grid has a mean height or depth between 0.2 and 1.0 mm.

The bioactive material used preferably is a bio-glass ceramic. It is, however, also possible to use other bioactive materials, such as a bioactive composite or apatite-containing sinter products. Finally, it is also possible to make the prosthesis of the invnention of a core material with a coating of bioactive substances. According to a further embodiment of the invention, the auditory wall prosthesis may comprise merely a part of the overall sleeve, in particular, a circumferential sleeve section or a part of it.

The object of the invention is attained a prosthesis of the aforementioned type in that the prosthesis contains an insoluble bioinert material, in at least part of its surface area or is provided with a partial coating of an insoluble bioinert material. The coating may comprise an additively applied protective layer with a thickness of 0.25 to 10 $\mu$m, or at least one subtractively produced coversion layer with a thickness of 0.25 to 5 $\mu$m. It is further possible to constitute the coating of at least one conversion layer produced on the side of the prosthesis core and at least one additively applied protective layer resting on this conversion layer. Advantageously, at least the inner wall and/or the outer wall of the sleeve comprise an insoluble, bioinert material. However, the longitudinal sides of the sleeve may also consist of an insoluble, bioinert material. The bioinert material or the bioinert layer may comprise at least one of the following substances: metals, such as gold, platinum, titanium and metal alloys; carbon in suitable modifications, such as pyrolytic carbon (graphite); carbon compounds such as silicon carbide (SiC), titanium carbide (TiC), boron carbide ($B_4C$); special ceramic materials such as hexagonal boron nitride (BN), titanium nitride (TiN), silicon nitride ($Si_3N_4$); partially crystalline inorganic compound systems, such as enamels; inorganic single component (for example flint glass) or multicomponent glasses; oxides, such as titanium oxide ($TiO_2$) zirconium dioxide ($ZrO_2$) and aluminum oxide ($Al_2O_3$). According to an advantageous embodiment, the bioinert material or the bioinert layer comprises a residual bioglass-ceramic, bioceramic or bioglass free of apatite. The bioinert material, or the bioinert layer may also comprise a silane layer.

According to the process of the invention, the partial areas of the sleeve to be treated are exposed with the controlled supply of material, to a subsequent surface treatment to produce at least one additively applied, permanently attached bioinert protective layer acting in vivo as a biochemical barrier layer. It is, however, also possible to provide a coating process whereby the partial areas of the sleeve or a part of the sleeve involved are exposed by means of a controlled removal or exchange of materials to a chemical post-treatment to produce at least one subtractively obtained, permanently adhering bioinert conversion (leached) layer, acting in vivo as a biochemical barrier layer. The additive protective layer may be applied preferably by at least one of the following process steps: galvanizing or vapor deposition, sputtering, precipitation from organic solutions or vapor deposition in a vacuum; immersion, spraying or sprinkling with a subsequent heat treatment; immersion in water glass with subsequent heating to approximately 400° C. or immersion coating in a single or multicomponent melt mixture; simultaneous vapor deposition or vapor deposition of metals with a subsequent oxidizing treatment.

The substractive protective layer may be obtained according to the invention by treating the circumferential surface to be coated with aqueous acid solution or aqueous salt solutions with normalities between 0.001 and 0.1, for 5 min to 3 h, at temperatures between 20 to 100° C. As the aqueous acid solution 0.1 to 0.001 normal hydrochloric acid (HC1) or as the aqueous salt solution a 0.001 to 0.25 normal standard acetate buffer solution may be used. Finally, it is possible to expose the coated parts of the prosthesis subsequently to a thermal sealing and/or silanizing treatment.

Further objects, features and advantages of the present invention will become apparent from the detailed description of preferred embodiments which follows, when considered together with the attached figures of drawing.

BRIEF DESCRIPTION OF THE DRAWINGS

In the drawings, examples of embodiments of the invention are shown schematically. In the drawings:

FIG. 4a is a view similar to that of FIG. 1 (the line grid of the inner wall has been omitted for the sake of clarity), wherein the inner and the outer walls have additive protective layers;

FIG. 4b is a section through the object shown in FIG. 4a along the line A—A;

FIG. 5a is a view corresponding to FIG. 1, but with a supplemental additive coating of the two longitudinal lateral sides of the sleeve;

FIG. 6 is the object shown in FIG. 4b, but with a substractive layer; and

FIG. 7 is the object shown in FIG. 6, but with an additional substractive coating on the longitudinal lateral sides of the sleeve.

DETAILED DESCRIPTION OF PREFERRED EMBODIMENTS

Figure 1:
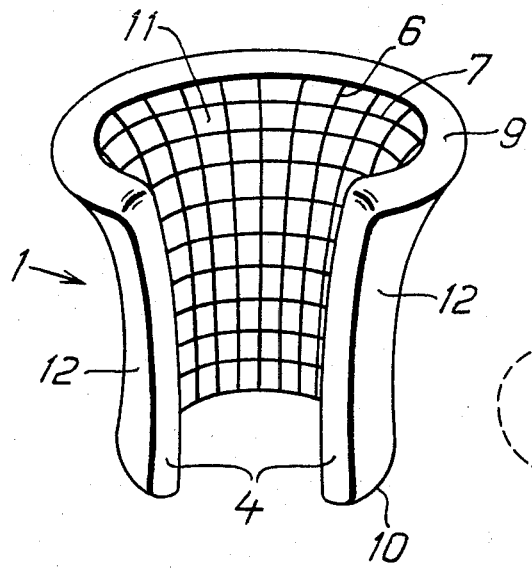
FIG. 1 shows a perspective view of a total auditory canal wall prosthesis ("sleeve")

FIG. 1 shows a total auditory canal wall prosthesis according to the invention in a perpspective, enlarged form. To describe the complex geometrical spatial form, reference is made initially to the schematic representations of FIG. 2a and 2b.

Figure 2A:
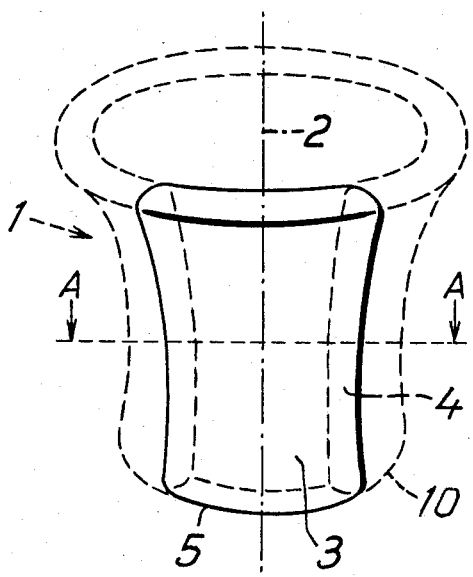
FIG. 2a is a view that is similar in principle to FIG. 1, but with a graphical emphasis on the sleeve's cut-out section.
Figure 2B:
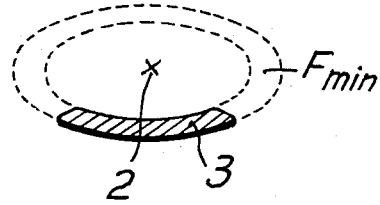
FIG. 2b is a section through the object of FIG. 2a along the line A—A.

If the front section of FIG. 2a is imagined to also be present in a broken line representation, the resultant structure is in a closed, hollow cylindrical sleeve with a cross-sectional surface deviating from the circular. If a plurality of sections is effected through the sleeve, the surfaces of immediately adjacent sections have different surface areas. In FIG. 2b the surface with a minimum surface area $F_{min}$ is shown; it is produced by a section along the line A—A in FIG. 2a.

As shown in FIG. 2a, the closed sleeve is more expanded in its upper area—i.e., in the direction of the upper sleeve rim 9—than in its lower area. The sectional surface areas, to which the sleeve axis 2 is always perpendicular, are not necessarily an ellipse in a strictly mathematical sense, as shown in FIG. 2b in an idealized form; rather, similar geometrical configurations are possible, for example, "distorted" circles or ellipses, weakly egg-shaped contours or similar, combined, closed formations. However, a characteristic of the initial geometric configuration is the slight contraction present in the center area of the sleeve and the differential expansion in the two terminal areas.

Beginning with this closed, hyperboloid hollow shape, the final prosthesis configuration according to the invention is obtained for a total implant, by effecting two "cuts" in an essentially axial direction and removing the sleeve's cut-out section 3 obtained in this manner, so that the open sleeve form shown in FIG. 1 is obtained.

As seen in FIG. 2a, the (axial) longitudinal lateral sides 4 of the sleeve 1 or the sleeve's cut-out section 3 are larger than their mean peripheral distance 5. The minimum peripheral distance may be recognized from the shaded part of FIG. 2b. The maximum peripheral distance is located in the upper area of the sleeve, which exhibits the greatest expansion. If one imagines a plane placed on each of the upper and lower terminal areas, i.e., on the corresponding sleeve rims 9 and 10 of the broken-line sleeve in FIG. 2a, the sleeve axis 2 would not be perpendicular to these imaginary planes. Preferably, the two planes are not exactly parallel to each other. Their distance from each other is larger in the area of the sleeve section 3 than in the opposite area (the rear area in FIG. 1) of the sleeve. This yields a final configuration of the sleeve which in its frontal lower area has a number of collar tip-like extensions.

The wall thickness of the sleeve 1 is essentially constant. However, slight beads or thickenings are possible in its terminal areas.

A characteristic according to the invention of the auditory canal wall prosthesis comprises that it has a grid—preferably over the entire area of its inner wall 11—including two families of lines 6 and 7, crossing each other. In the case shown, the lines 6 of the first family extend hyperbolically in the axial direction, and the lines 7 of the second family extend elliptically in the peripheral direction, so that the lines of the two systems intersect approximately at an angle of 90°. Even though in FIG. 1 for reasons of graphical simplification only lines are shown, in reality these are relief-like, three-dimensional markings. They may consist of recesses in the inner side 11 of the sleeve, for example grooves or flutes. The cross section of these preferably identical recesses may be rectangular, square, tub shaped, acutely angled, etc. However, relief-like protrusions may also be applied to the inner side of the sleeves, for example, beads.

In place of continuous embodiments with linear configurations, both positive (relief-like) and negative (recesses) discontinuous families of lines may be provided, for example, (positive) knobs or (negative) pits. In all of these cases it is true with regard to the dimensioning of the coordinate grid that its mesh width is at least twice as large as the transverse dimension of the positive or negative "lines". Grids different from those shown in FIG. 1—for example, with a rhomboid mesh—are also possible.

By the application of a relief-like or waffled grid 6, 7 in, or to the inner wall 11 of the prosthesis 1, the overall duration of bone surgery may be substantially shortened. The surgeon is now able to prepare an implant configuration that is optimally fitted and corresponds to the individual requirements of the patient by means of a few preoperational fitting experiments, specifically by introducing the total implant in the area of the auditory canal wall which is to be reconstructed surgically, and by simultaneously estimating the areas of the prosthesis to be removed subsquently by grinding. In view of the complex anatomy of the outer and middle auditory tract, the severely restricted observational possibility of the surgeon during the introduction of the implant in the rear area of the auditory canal, and in view of the small dimensions of of the human auditory canal compared with normal surgical conditions, it is significant progress to be able to prepare the exact contour of of the permanent implant to be inserted by "fittings" to be effected a few times.

It may be derived from the foregoing that the shape and size of the embodiment of the lines should preferably be such that, for the purpose of the better illumination of the location of the implant during the preoperative fitting, the illuminating light will cause the formation of shadows by the families of lines of the grid. An inclined illumination of this type emphasizes the relief character of the grid.

Experiments have shown that a grid with (negative) recesses is more advantageous than one with (positive) beads or knobs, since in the case of the latter certain changes may result in misinterpretation in the course of a postoperative inspection.

For manufacturing reasons, but primarily for overriding immunological considerations, the positive grid markings comprise the same biomaterial as the prosthesis itself. In the case of negative grid markings, no additional optical contour reinforcements, possibly of a different color, are provided.

A bioactive glass-ceramic may be used as the material, such as that described in detail in German Pat. No. 23 26 100. Other suitable materials are bioactive composites based on apatite-containing sinter products, known from German Pat. No. 23 46 739 and German Pat. No. 24 34 979. Polymeric bioactive composite materials are further usable, such as those protected by German Pat. No. 25 01 683. Finally, it is possible, in principle, to provide a core material comprising a known bio-inert substance, or with a total or partial coating of a bioactive material, as described, for example, in Austrian Pat. No. 347 023.

Figure 3:
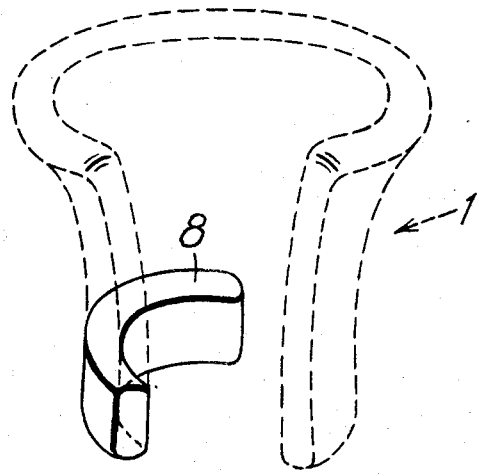
FIG. 3 is a view similar to principle to FIG. 1, but with graphical emphasis on a part of the sleeve section (partial auditory canal wall prosthesis)

In FIG. 3, the sleeve 1 shown in FIG. 1 is again represented by the broken line. A part 8 of the sleeve is shown by a solid line. This is understood to be a peripheral sectional part essentially perpendicular to the sleeve axis 2. Obviously, in keeping with the intended application, various other configurations of sleeve sections or cutouts of or from the total prosthesis provided as a spatial shape, are possible.

In FIG. 3 merely a part of such a sleeve section is shown. This part 8 represents a partial implant for the partial reconstruction of the rear portion of the auditory canal wall. For reasons of clarity the internal grid, which is actually present, is omitted.

The use of biomaterials as the material for the prosthesis according to the invention offers particular advantages in the field of middle ear surgery; these are described in detail in the German Patent Application No. P 30 36 245.9.

It is known that bioactive bone replacement materials—particularly bioglass or bioglass-ceramics—exhibit a certain surface solubility, which presumably is a necessary condition for the development of the bone/implant composite. On the other hand, this specific property under particularly unfavorable local anatomical conditions, such as particularly those present in the implantation of a prosthesis in soft tissue or the contacting of such a prosthesis with soft tissue, may lead to interference with the long term stability of the implant. As the property of bioactivity is obtained by the specific chemical composition of the implant material, such a material is *not* particularly advantageous for implantation in *other* tissues. It may be observed for example that the implantation of a bioactive material generates reactions of stronger sensitivity in soft tissue than a bioinert material.

Since the auditory canal wall prosthesis according to the invention is always in contact will osseous tissue in the area of the upper and lower sleeve rim 9 and 10, these surface areas are not bio-inactivated. In contrast, the inner wall 11 and/or the outer wall 12 and/or the two longitudinal lateral sides 4 may be provided in part or completely with a bioinert, insoluble protective layer.

In FIG. 4a, such a layer—in particular an additive protective layer S(+)—is shown. It covers the inner wall (combined reference symbol: "11(S+)") and the outer wall 12 (combined reference symbol: "12(S(+))". As the protective layer S(+) achieves its inactivating effect even with very slight layer thicknesses, the application of such an additive coating will not optically "obscure" the grid present on the basic shape.

In FIG. 5a and 5b an additively coated embodiment is shown, in which the longitudinal sides 4 of the sleeve 1 have also been made bioinactive.

FIG. 6 shows a section on the imaginary line A—A of a sleeve with a geometrically nonaddititive, bioinert, insoluble, subtractive layer S(−) on the inner wall 11 and the outer wall 12 (combined reference symbol: "11(S(−))" and "12(S(−))"). FIG. 7 shows an example in which the longitudinal sides are also coated subtractively ("4(S(−))").

Both of the protective layers —additive and subtractive—S(+) and S(−) are equivalent with respect to their function. They represent in a certain sense biochemical "corrosion" protection layers, assuring the presence of complete transport and passage barriers for any exchange of a substance (ions) between the chemical components of the implants and the components of the physiological-biochemical body fluids.

For example, a subtractive protective layer S(−) may be obtained in vitro. In the case of an implant comprising a solid bioglass-ceramic material or a bioglass material, the surface area which necessarily come into permanent contact with soft tissue—ie., because of anatomical conditions or as intended by the ear surgeon, for example, in the lining of certain implant areas with epithelial tissue—, are chemically pretreated. Thus, aqueous acid solutions and/or aqueous salt solutions, in normalities between 0.001 to 0.1, attack the original bioglass-ceramic surface. Attack (dissolution or leaching) reactions and exchange reactions occur side by side, with the consequence that initially a depletion and finally the complete destruction (conversion) of a phase—in particular of the crystalline component or components—of the glass-ceramic composite system take place. However, bases or buffer systems may also be used for the chemical attack, which, as a function of their actual chemistry, their concentration and their $p_H$ value, act in a controlled manner on certain phase components of the bioglass-ceramic "composite system", thereby effecting the change in properties of the implant surface desired.

The glass-ceramic remaining after this combined chemical treatment, depleted of its apatite component, shall be designated a "residual bioglass ceramic". With regard to its chemical properties, it is insoluble, free of pores and prevents any transport of ions; with respect to its biochemical-physiological action, it is bio-inactive, i.e., bio-"inert"; and, with respect to its mechanical properties it is abrasion resistant and adherent to the core material of the prosthesis. As seen in FIGS. 6 and 7, the production of a subtractive layer S(−) does not change the total volume of the implant. Rather, chemical exchange or conversion processes take place in the surface areas, which are directed "inwardly" to a certain extent. In contrast, the additive layers S(+) shown in FIG. 4a–5b are located on the surface of the implant, so that the overall volume of the coated prosthesis (FIGS. 4a and 5a) is slightly higher.

If necessary, the subtractive layer S(−) may be additionally densified or sealed thermally. Beyond this, in the area of the bio-inert coating, a silane layer may be additionally applied.

It is therefore possible by means of the prosthesis according to the invention to reconstruct all of the different partial areas or the entire rear tract of a human auditory canal wall—beginning with an existing total implant—in an anatomically correct manner, permanently and within a very short period of time.

We claim:

1. A prosthesis for the total or partial replacement of a rear auditory canal wall, comprising:
    an open ended, hollow cylindrical sleeve having a longitudinal axis extending between a first and a second end, said sleeve including a wall defining an inner surface and an outer surface, wherein said inner surface is defined by a plurality of differential hyperboloid expansions having ellipsoidal cross sections perpendicular to said longitudinal axis, wherein at least one first expansion defines said first end and at least one second expansion defines said second end;
    said sleeve further including a cut-out section defined by first and second axial edges extending from said first end to said second end; and
    said sleeve including a bioactive material.

2. A prosthesis as recited in claim 1, wherein said inner section of said wall comprises means forming a spatial coordinate grid.

3. A prosthesis as recited in claim 2, wherein said means comprise a first family of lines, and a second family of lines, wherein the first family of lines crosses the second family of lines.

4. A prosthesis as recited in claim 3, wherein said first family of lines comprises a plurality of hyperbolic lines extending substantially in the direction of said longitudinal axis, and wherein said second family of lines comprises a plurality of elliptical lines extending substantially perpendicular to said longitudinal axis.

5. A prosthesis as recited in claim 3, wherein said families of lines comprise a plurality of recesses.

6. A prosthesis as recited in claim 5, wherein said recesses comprise a shape selected from the group consisting of: triangular, rectangular and rounded.

7. A prosthesis as recited in claim 2, wherein said families of lines comprises a plurality of bead-like protrusions.

8. A prosthesis as recited in claim 2, wherein said means comprise a discontinuous arrangement of dimples.

9. A prosthesis as recited in claim 2, wherein said means comprise a discontinuous arrangement of nubs.

10. A prosthesis as recited in claim 2, wherein the means comprise the same bioactive material said sheeth comprises.

11. A prosthesis as recited in claim 2, wherein the means comprise a mean mesh width from about 1 mm to about 2 mm.

12. A prosthesis as recited in claim 2, wherein a first ellipse having a principle axis and having an open section is described by an intersection of said sheeth and a plane perpendicular to said long axis, wherein said open section of said ellipse corresponds to said cut-out section of said sheeth, wherein a projection of said ellipse from a point corresponding to said first axial edge to a point corresponding to said second axial edge defines a first circumferential distance, wherein the circumferential distance is less than the length of said first and second edges, wherein a plurality of ellipses may be defined in the manner of said first ellipse and wherein a shortest principle axis of said plurality of ellipses is greater than a mean circumferential distance of said plurality of ellipses.

13. A prosthesis as recited in claim 1, wherein an axial length of said sleeve measured along said longitudinal axis increases from a minimum opposite said cut-out section to a maximum at said first and second axial edges.

14. A prosthesis as recited in claim 12, wherein a mean axial length of said sleeve is between about 12 mm and about 25 mm, wherein a mean first circumferential distance of said ellipses is between about 7 mm and about 14 mm, wherein said wall has a thickness of between about 0.5 mm and about 20 mm, wherein a mean length of principle axes of said ellipses is between about 10 mm and about 17 mm.

15. A prosthesis as recited in claim 14, wherein said means are a relief structure having a mean height of between about 0.2 mm to about 1.0 mm.

16. A prosthesis as recited in claim 1, wherein said bioactive material comprises a composite material.

17. A prosthesis as recited in claim 1, wherein said bioactive material comprises apatite-containing sinter products.

18. A prosthesis as recited in claim 1, wherein said bioactive material comrpises a glass ceramic.

19. A prosthesis as recited in claim 1, wherein said sleeve comprises a core material and a coating of bioactive substance.

20. An auditory canal wall prosthesis, comprising a section of the sleeve according to claim 1.

21. A prosthesis as recited in claim 1, further comprising an insoluble bio-inert material exposed on at least part of the surface area of said sleeve.

22. A prosthesis as recited in claim 1, further comprising a partial coating of an insoluble bio-inert material.

23. A prosthesis as recited in claim 22, wherein said coating comprises at least one additive layer having a thickness of between about 0.25 $\mu m$ and 5 $\mu m$.

24. A prosthesis as recited in claim 22, wherein said coating comprises at least one subtractively produced conversion layer having a thickness between about 0.25 μm and about 5 μm.

25. A prosthesis as recited in claim 22, wherein said partial coating comprises at least one subtractively produced conversion layer on said core material and at least one additive protective layer on said conversion layer.

26. A prosthesis as recited in claim 21, wherein said inner surface of said wall comprises an insoluble bio-inert material.

27. A prosthesis as recited in claim 21, wherein said outer surface of said wall comprises an insoluble bio-inert material.

28. A prosthesis as recited in claim 21, wherein said outer and inner surfaces of said wall comprise an insoluble, bio-inert material.

29. A prosthesis as recited in claim 28, wherein said first and second edges comprise an insoluble, bio-inert material.

30. A prosthesis as recited in claim 21, wherein said bio-inert material includes at least one constituent selected from the group, consisting of:
(a) metals such as gold, platinum, titanium and metal alloys;
(b) carbon in its appropriate modifications, such as pyrolytic carbon (graphite);
carbon compounds, such as silicon carbide (SiC), titanium carbide (TiC), boron carbide (B$_4$C);
(c) special ceramic materials, such as hexagonal boron nitride (BN), titanium nitride (TiN), silicon nitride (Si$_3$N$_4$);
(d) partially crystalline inorganic composite systems, such as enamels;
(e) inorganic single component (for example flint glass) or multi-component glasses; and
(f) oxides such as titanium dioxide (TiO$_2$), zirconium dioxide (ZrO$_2$) and aluminum oxide (Al$_2$O$_3$).

31. A prosthesis as recited in claim 20, wherein said bio-inert material is selected from the group consisting of:
residual bioglass ceramic;
bioceramic; and
bioglass free of apatite.

32. A prosthesis as recited in claim 31, wherein said bio-inert material further comprises a silane layer.

33. A method for the total replacement of a rear auditory canal wall using a prosthesis comprising an open ended, hollow cylindrical sleeve having a longitudinal axis extending between a first and a second end, said sleeve including a wall defining an inner surface and an outer surface wherein said inner surface is defined by a plurality of differential hyberboloid expansions having ellipsoidal cross sections perpendicular to said longitudinal axis, wherein at least one first expansion defines said first end and at least one second expansion defines said second end; said sleeve further including a cut-out section defined by first and second axial edges extending from said first end to said second end; and said sleeve including a bioactive material; wherein the method comprises the steps of:
preparing the prosthesis for implantation; and implanting the prosthesis.

34. A method for the partial replacement of a rear auditory canal wall comprising the steps of claim 33 and further comprising, before said step of preparing the step of producing an appropriate section of the prosthesis.

35. A prosthesis as recited in claim 14, wherein said means are a recess structure having a mean depth of between about 0.2 mm and about 1.0 mm.

* * * * *